United States Patent
Babic et al.

(10) Patent No.: US 9,314,793 B2
(45) Date of Patent: Apr. 19, 2016

(54) ANALYTICAL AIDS WITH HYDROPHILIC COATING CONTAINING NANOPARTICLES WITH SILICA STRUCTURE AND METHODS OF PRODUCING AND USING THE SAME

(71) Applicant: Roche Diabetes Care, Inc., Indianapolis, IN (US)

(72) Inventors: Branislav Babic, Mannheim (DE); Peter Greiwe, Heidelberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 106 days.

(21) Appl. No.: 14/027,656

(22) Filed: Sep. 16, 2013

(65) Prior Publication Data
US 2014/0017123 A1 Jan. 16, 2014

Related U.S. Application Data

(63) Continuation of application No. PCT/EP2012/054993, filed on Mar. 21, 2012.

(30) Foreign Application Priority Data

Mar. 22, 2011 (EP) .................................. 11159172

(51) Int. Cl.
*B01L 3/00* (2006.01)
*A61B 5/15* (2006.01)
*A61B 5/151* (2006.01)
*C09D 7/12* (2006.01)

(52) U.S. Cl.
CPC ................. *B01L 3/56* (2013.01); *A61B 5/1411* (2013.01); *A61B 5/15142* (2013.01); *C09D 7/1225* (2013.01); *A61B 2562/0295* (2013.01); *Y10T 428/2982* (2015.01)

(58) Field of Classification Search
CPC .... B01L 3/56; C09D 7/1225; A61B 5/15142; A61B 5/1411; A61B 2562/0295; Y10T 428/2982
See application file for complete search history.

(56) References Cited

U.S. PATENT DOCUMENTS

| | | |
|---|---|---|
| 4,235,638 A | 11/1980 | Beck et al. |
| 2007/0179373 A1 | 8/2007 | Pronovost |
| 2008/0103415 A1 | 5/2008 | Roe et al. |
| 2010/0209613 A1 * | 8/2010 | Rong et al. ............. 427/387 |

FOREIGN PATENT DOCUMENTS

| | | |
|---|---|---|
| EP | 1358896 A1 | 11/2003 |
| EP | 1887355 A1 | 2/2008 |
| EP | 1894525 A1 | 3/2008 |
| EP | 2014727 A1 | 1/2009 |
| WO | 2008/015227 A1 | 2/2008 |
| WO | 2009/095184 A1 | 8/2009 |
| WO | 2009/095343 A1 | 8/2009 |
| WO | 2010/045247 A1 | 4/2010 |

* cited by examiner

*Primary Examiner* — Lore Jarrett
(74) *Attorney, Agent, or Firm* — Woodard, Emhardt, Moriarty, McNett & Henry LLP

(57) ABSTRACT

Disclosed herein are analytical aids having a surface coated at least partially with a hydrophilic coating, where the hydrophilic coating includes nanoparticles with silica structure and an average particle size in a range from about 1 nm to about 500 nm. Also disclosed are methods of producing the analytical aids, as well as using the analytical aids in, for example, a sampling device containing the at least partially coated analytical aid.

24 Claims, 1 Drawing Sheet

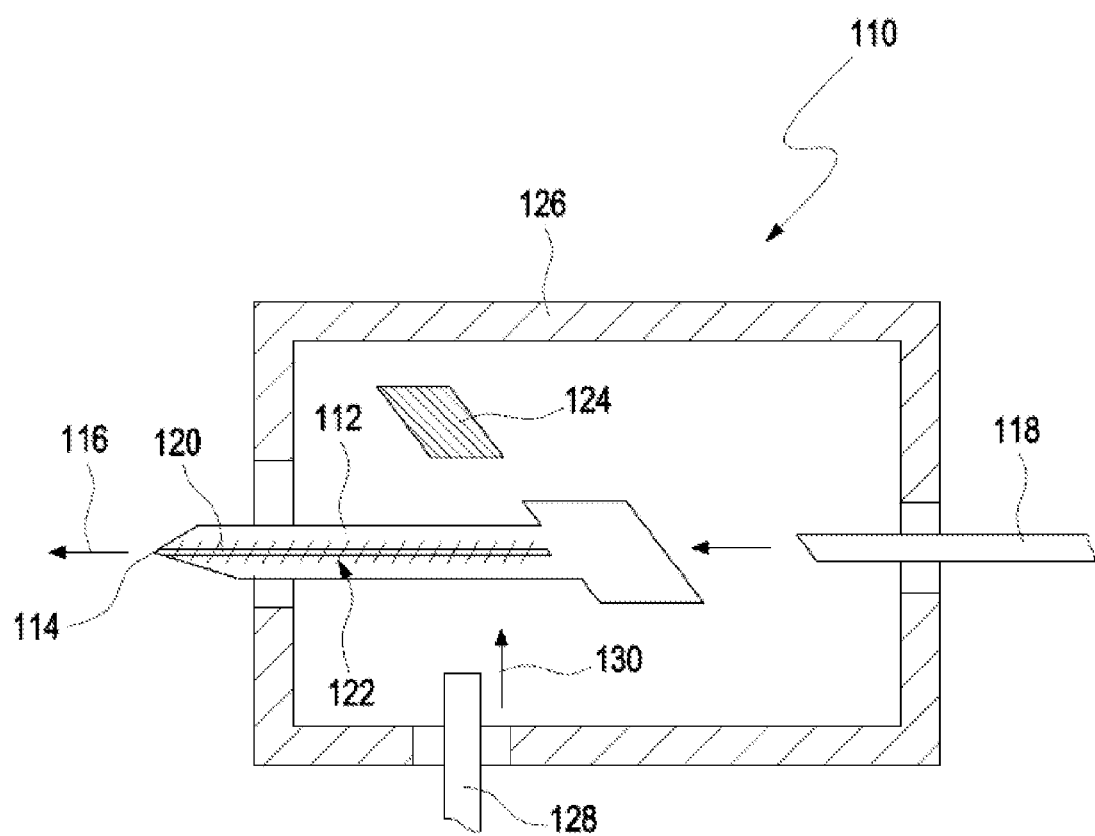

ANALYTICAL AIDS WITH HYDROPHILIC COATING CONTAINING NANOPARTICLES WITH SILICA STRUCTURE AND METHODS OF PRODUCING AND USING THE SAME

CROSS-REFERENCE TO RELATED APPLICATIONS

This patent application is a continuation of Int'l Patent Application No. PCT/EP2012/054993; filed 21 Mar. 2012, which claims the benefit of EP Patent Application No. 11159172.3; filed 22 Mar. 2011. Each patent application is incorporated herein by reference as if set forth in its entirety.

TECHNICAL FIELD

The disclosure relates generally to engineering and chemistry, and more particularly to analytical aids having a surface coated at least partially with a hydrophilic coating, where the hydrophilic coating contains nanoparticles with silica structure. The disclosure also relates to methods of producing the analytical aids. The disclosure further relates to uses of the hydrophilic coating in, for example, sampling devices including at least a partially coated analytical aid.

BACKGROUND

A great many analytical aids are known for rapid and quantitative analytical determination of constituents of liquid samples. The analytical aids can be in the form of individual test elements such as test strips or strip-shaped test materials, as well as in integrated systems in which the testing element is a part of a sampling device. For reasons of simplified and more economical production and component stability, such analytical aids typically are made of plastic or metal and generally have a comparatively hydrophobic surface, which is a disadvantage for rapid and uniform wetting of the analytical aid with liquid samples.

Int'l Patent Application Publication No. WO 2007/045412 describes sampling devices for collecting body fluids that have a needle element and that are equipped with a testing element, with which at least one analyte in the body fluid can be detected qualitatively or quantitatively. In this case, the body fluid sample is transported along the needle element to the testing element. Because the site of insertion of the needle element into the skin is disposed at some distance from the testing element, the body fluid sample must travel a few millimeters (mm) along the capillary to reach the testing element. The needle elements are made of steel and therefore have a relatively hydrophobic steel surface and thus are not very suitable for transporting the body fluid sample.

For the purpose of increasing the flow rate of the body fluid sample along the needle element, EP Patent Application Publication No. 2025287 describes modifying the surface of the needle element with a hydrophilic coating. Non-ionic surfactants, such as polysorbate, are mentioned for use as the hydrophilic coatings.

Similarly, EP Patent Application Publication No. 2014727 describes hydrophilizing metal-oxide coatings such as, for example, AlOOH, $TiO_x$, $SiO_2$ or the like. The metal-oxide coatings can be applied and fixed in the form of discrete particles in suspensions. The use of organic polymer compounds such as, for example, PVP-PEG, and of water-soluble organic poly-acids and/or salts thereof such as, for example, PAA or heparin salts, as the hydrophilic coating, also is known.

For forming a hydrophilic surface of the needle element, hydrophilization by physicochemical means also is possible. For example, etching of a steel surface or a plasma or corona treatment can be used to create active metal surfaces. Unfortunately, these effects are temporary, and therefore only are auxiliary measures for preparing the needle element surface for subsequent coating.

Likewise, a capillary-active surface structure can be provided to improve the transport of the body fluid sample along the needle element, where a hydrophilic coating of the capillary surface structure can be especially advantageous for speed of transport of the body fluid along the needle element.

In this manner, EP Patent Application Publication No. 1887355 describes a needle element designed as a microfluidic system for capillary transport of a body fluid sample and a method of applying a hydrophilic surface coating on the needle element. Polyacrylic acid, polyacrylate, dextran sulphate and/or chondroitin sulphate are mentioned for use as the hydrophilic surface coating materials. To ensure rapid and reliable transport of the body fluid sample along the needle element, a surface structure is further described that can be formed as a microchannel on the needle element with the hydrophilic surface coating.

However, the known coating materials demonstrate inadequate stability, in particular, they have inadequate long-term stability. One reason for the inadequate stability includes insufficient bonding of the coating to the surface of the substrate, which may result in detachment of the coating during the coating process, during storage or during use of the substrate such as, for example, when a needle element coated in this way is inserted into the skin. Another reason is that the hydrophilic coating may not even be resistant to longer storage at room temperature or to temperature fluctuations. Moreover, some compounds display low stability when exposed to sterilization conditions and/or low resistance to gas evolution from packaging.

In particular, instability with respect to packaging materials often means that in the case of substrates packaged in plastic materials, the hydrophilicity of the coated surfaces decreases markedly during storage and sufficient hydrophilicity of the substrates after storage is no longer guaranteed. This loss of hydrophilicity can be explained by adsorption of volatile, nonpolar constituents of the packaging materials.

To prevent such loss of hydrophilicity, Int'l Patent Application Publication No. WO 2008/015227 describes using specific packaging that contains a loose covering for the hydrophilic coating and/or the addition of adsorbents in the packaging to prevent absorption of volatile constituents by the hydrophilic coating. Unfortunately, the packaging is complicated, expensive and, in particular, is disadvantageous for measuring equipment with automatic operation, which also must provide reliable unpacking of the substrate from the packaging.

US Patent Application Publication No. 2007/0179373 describes apparatuses and methods for collecting a body fluid sample. It discloses inter alia an integrated collection device having an analyte detector and a gradient means to drive the transport of the body fluid from a point of contact to a point of detection. The integrated collection device has a layered structure that includes multiple layers and features a first layer and a second layer that forms a surface layer. A hydrophilic surface is generated by powder coating the surface layer with fumed silica nanoparticles.

For the foregoing reasons, there is a need for analytical aids with hydrophilic coatings that have sufficient stability, in particular, sufficient stability even in the presence of volatile, nonpolar constituents of packaging materials.

BRIEF SUMMARY

The present disclosure is concerned with the problems noted above by providing analytical aids with a hydrophilic coating, which has advantageous wetting properties and is characterized by a high stability.

Surprisingly, it was found that the problems can be solved when nanoparticles with silica structure and an average particle size in the range from about 1 nm to about 500 nm are used for coating analytical aids. The coated analytical aids are characterized by advantageous hydrophilicity and wettability. Moreover, high stability of the coated analytical aids is provided.

Accordingly, and in one aspect, analytical aids are disclosed that include a surface coated at least partially with a hydrophilic coating, where the hydrophilic coating contains nanoparticles with silica structure and an average particle size, determined according to DIN ISO 22412:2008 (dynamic light scattering), in the range from about 1 nm to about 500 nm, where the nanoparticles include groups of structure (I) and/or structure (II):

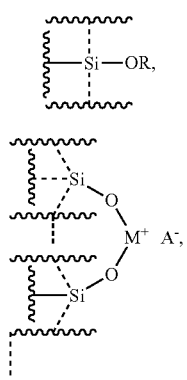

where in each of the groups of structure (I), independently of one another, R is selected from H, a metal-containing ion,

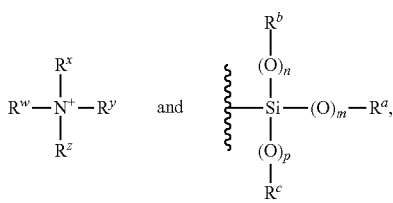

where $R^w$, $R^x$, $R^y$ and $R^z$, independently of one another, are selected from H and alkyl, where $R^a$, $R^b$ and $R^c$, independently of one another, are optionally substituted residues, selected from H, alkyl, aryl, heteroaryl, cycloalkyl, cycloheteroalkyl, alkenyl and alkoxyalkyl, where n, m and p, independently of one another, are 0 or 1, and where $M^+$ is a metal ion and $A^-$ is a physiologically compatible anion.

In contrast to the above, US Patent Application Publication No. 2007/0179373 discloses only a hydrophilic surface coating with fumed silica nanoparticles. The nanoparticles as described herein thus comprise groups of structure (I) and/or (II).

In another aspect, methods are disclosed for producing an analytical aid as described herein, where the method includes, but is not limited to, steps such as:
- a step of providing the analytical aid;
- a step of coating the analytical aid by bringing the analytical aid into contact with a mixture G of at least one dispersant and nanoparticles with silica structure, where the nanoparticles have an average particle size, determined according to DIN ISO 22412:2008, in the range from about 1 nm to about 500 nm, where the nanoparticles include groups of structure (I) and/or (II):

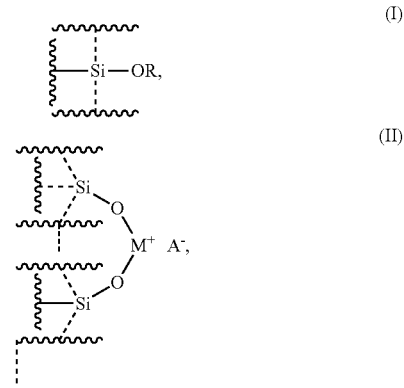

where in each of the groups of structure (I), independently of one another, R is selected from H, a metal-containing ion,

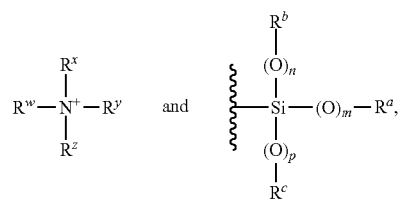

where $R^w$, $R^x$, $R^y$ and $R^z$, independently of one another, are selected from H and alkyl, where $R^a$, $R^b$ and $R^c$, independently of one another, are optionally substituted residues, selected from H, alkyl, aryl, heteroaryl, cycloalkyl, cycloheteroalkyl, alkenyl and alkoxyalkyl, where n, m and p, independently of one another, are 0 or 1, and where $M^+$ is a metal ion and $A^-$ is a physiologically compatible anion;
- a step of drying the analytical aid obtained in the previous step; and
- an optional step of sterilizing the analytical aid obtained in the previous step.

In one embodiment, the coating/contacting step includes dip coating and/or spray coating and/or contact coating, where the analytical aid and/or the surface of the analytical aid includes at least partially of a metal and/or a metal alloy and/or a metal oxide and/or a mixed metal oxide and/or a mixed metal oxide.

In another aspect, compositions including the nanoparticles described herein are disclosed.

In another aspect, uses of nanoparticles described herein are disclosed such as, for example, as a hydrophilic coating for a needle element or a testing element of a sampling device for collecting a body fluid, where the nanoparticles includes groups of structure (I) and/or structure (II):

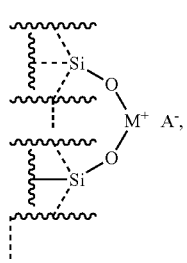

(II)

where in each of the groups of structure (I), independently of one another, R is selected from H, a metal-containing ion,

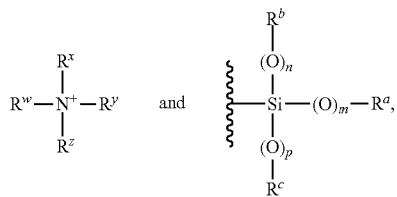

and where $R^w$, $R^x$, $R^y$ and $R^z$, independently of one another, are selected from H and alkyl, where $R^a$, $R^b$ and $R^c$, independently of one another, are optionally substituted residues, selected from H, alkyl, aryl, heteroaryl, cycloalkyl, cycloheteroalkyl, alkenyl and alkoxyalkyl, where n, m and p, independently of one another, are 0 or 1, and where $M^+$ is a metal ion and $A^-$ is a physiologically compatible anion.

These and other advantages, effects, features and objects of the invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 1 shows an exemplary sampling device.

While the present invention is susceptible to various modifications and alternative forms, exemplary embodiments thereof are shown by way of example in the drawings and are herein described in detail. It should be understood, however, that the description of exemplary embodiments that follows is not intended to limit the invention to the particular forms disclosed, but on the contrary, the intention is to cover all advantages, effects, features and objects falling within the spirit and scope of the invention as defined by the embodiments above and the claims below. Reference should therefore be made to the embodiments above and claims below for interpreting the scope of the invention. As such, it should be noted that the embodiments described herein may have advantages, effects, features and objects useful in solving other problems.

DESCRIPTION OF PREFERRED EMBODIMENTS

The analytical aids, methods of producing the analytical aids, compositions and uses thereof now will be described more fully hereinafter with reference to the accompanying drawing, in which some, but not all embodiments are shown. Indeed, the analytical aids, methods of producing the analytical aids, compositions and uses may be embodied in many different forms and should not be construed as limited to the embodiments set forth herein; rather, these embodiments are provided so that this disclosure will satisfy applicable legal requirements.

Likewise, many modifications and other embodiments of the analytical aids, methods of producing the analytical aids, compositions and uses thereof as described herein will come to mind to one of skill in the art to which the invention pertains having the benefit of the teachings presented in the foregoing descriptions and the associated drawing. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Nanoparticles

As noted above, the composition can be a hydrophilic coating that includes nanoparticles with silica structure and an average particle size, determined according to DIN ISO 22412:2008 (dynamic light scattering, which is a particle size analysis technique known to one of skill in the art), in the range from about 1 nm to about 500 nm.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

In some instances, the nanoparticles have a size in the range from about 1 nm to about 100 nm, from about 1 nm to about 50 nm, from about 3 nm to about 25 nm, or from about 5 nm to about 15 nm.

In some instances, the nanoparticles have a BET surface area in the range from about 100 m²/g to about 700 m²/g.

When compositions of the nanoparticles are used as a coating, as will be described in greater detail below, the coating can have an average layer thickness, also referred to as average thickness or mean thickness hereinbelow, of no more than about 500 nm or of no more than about 300 nm. The layer thickness can be measured by known methods such as, for example, by means of a destructive or a non-destructive method. More specifically, the layer thickness can be measured by means of an ellipsometer and/or by means of a scanning force microscope and/or by means of an "alpha stepper," which is a device that scans a surface of the layer by means of a stylus, the deflection and/or position of which is recorded. Other measurement methods also are contemplated.

Alternatively, or additionally, the average layer thickness can be calculated and/or determined semi-empirically. For example, the average layer thickness may be determined from a known thickness of the coating and a coating weight. Thus, calculated average layer thicknesses can be in the range from about 30 nm to about 300 nm or in the range from about 50 nm to about 150 nm. Fluctuations in one or more channels and/or capillaries and/or fluctuations due to edge effects need not be taken into account here.

As noted above, the structure of the nanoparticles with silica structure includes groups of structure (I) and/or structure (II):

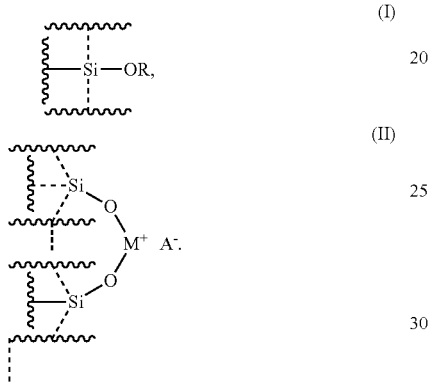

In some instances, at least a portion of the surface of the nanoparticles is modified with groups of structure (I) or groups of structure (II), particularly at least with groups of structure (I).

Analytical Aids and Methods of Producing the Same

As noted above, the analytical aids include at least one surface coated at least partially with a hydrophilic coating, where the hydrophilic coating contains nanoparticles with silica structure that can include groups of, for example, structure (I). Briefly, the analytical aids can be produced by coating the at least one surface with a mixture G that includes at least one dispersant and nanoparticles with silica structure, as described above, where the nanoparticles have groups of structure (I).

Groups of Structure (I):

As noted above, the residue R can be selected from H, a metal-containing ion,

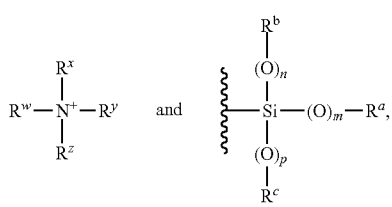

where $R^w$, $R^x$, $R^y$ and $R^z$, independently of one another, are selected from H and alkyl, where $R^a$, $R^b$ and $R^c$, independently of one another, are optionally substituted residues, selected from H, alkyl, aryl, heteroaryl, cycloalkyl, cycloheteroalkyl, alkenyl and alkoxyalkyl, and where n, m and p, independently of one another, are 0 or 1.

When R is H, the silica particles can be groups of structure

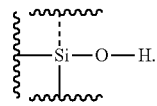

In view thereof, the analytical aids can include a surface coated at least partially with a hydrophilic coating, where the hydrophilic coating contains nanoparticles with silica structure, which include groups of structure

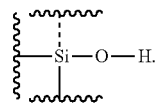

Such an analytical aid can be made via a coating step with a mixture G that includes at least one dispersant and nanoparticles with silica structure, as described above, where the nanoparticles have groups of structure

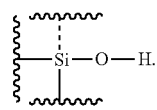

Alternatively, R can be a metal-containing ion. In this instance, the silica particles can contain groups of structure

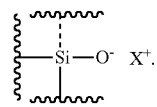

In some instances, $X^+$ is an alkaline-earth metal containing ion, such as $Mg^{2+}$ or $Ca^{2+}$, an alkali metal ion or an aluminium containing ion.

When R is an alkali metal ion, the nanoparticle can contain groups of structure

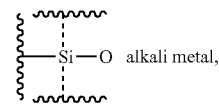

or the structure

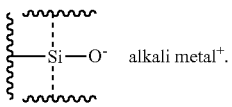

In some instances, the alkali metal can be selected from $Li^+$, $Na^+$, $K^+$ and mixtures thereof.

As used herein, "mixtures thereof" means that in each individual group of structure

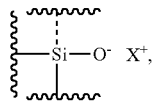

$X^+$, independently of each $X^+$ contained in each further group of structure Si—O—$X^+$ contained in the silicon nanoparticle, can be selected from

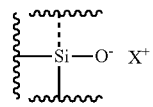

containing $X^+$ selected from $Li^+$, $Na^+$ and $K^+$, and therefore the nanoparticles can in each case have several different alkali metal counter-ions. In certain instances, $X^+$ is $Na^+$.

It is further contemplated that an analytical aid as described herein includes a surface coated at least partially with a hydrophilic coating, where the hydrophilic coating contains nanoparticles with silica structure, which include groups of structure

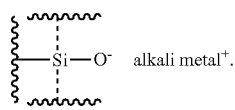

Such an analytical aid can be made via a coating step with a mixture G that includes at least one dispersant and nanoparticles with silica structure, as described above, wherein the nanoparticles have groups of structure

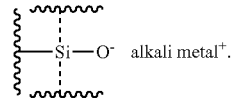

Alternatively, R can be a cation of the following structure

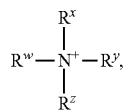

where $R^w$, $R^x$, $R^y$ and $R^z$, independently of one another, are selected from H and alkyl.

As used herein, "alkyl" means linear or branched, optionally substituted alkyl residues.

If $R^w$ and/or $R^x$ and/or $R^y$ and/or $R^z$ is an alkyl residue, the alkyl residue can be selected from methyl, ethyl, propyl, iso-propyl, butyl, sec-butyl and tert-butyl, particularly methyl.

If R is

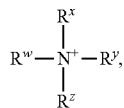

then $R^w$, $R^x$, $R^y$ and $R^z$, independently of one another, are selected from H, methyl and ethyl. In some instances, $R^w$, $R^x$, $R^y$ and $R^z$ are H.

It is further contemplated that an analytical aid as described herein includes a surface coated at least partially with a hydrophilic coating, where the hydrophilic coating contains nanoparticles with silica structure, which include groups of structure

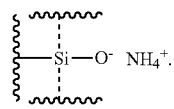

Such an analytical aid can be made via a coating step with a mixture G that includes at least one dispersant and nanoparticles with silica structure, as described above, where the nanoparticles have groups of structure

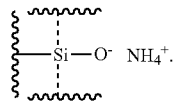

The nanoparticles can be obtained, for example, under the name Ludox® AS-30 (Grace, Aldrich) or Levasil® 200 N/30%. (EKA).

In some instances, R is

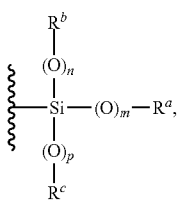

where $R^a$, $R^b$ and $R^c$, independently of one another, are optionally substituted residues, selected from H, alkyl, aryl, heteroaryl, cycloalkyl, cycloheteroalkyl, alkenyl and alkoxyalkyl, and where n, m and p, independently of one another, are 0 or 1.

Alternatively, R is

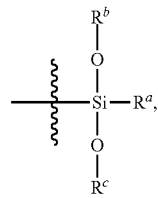

where p and n are 1 and m is 0.

It is further contemplated that an analytical aid as described herein includes a surface coated at least partially with a hydrophilic coating, where the hydrophilic coating contains nanoparticles with silica structure, which include silane-modified silicon groups of structure

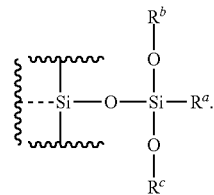

Such an analytical aid can be made via a coating step with a mixture G that includes at least one dispersant and nanoparticles with silica structure, as described above, where the nanoparticles have silane-modified silicon groups of structure

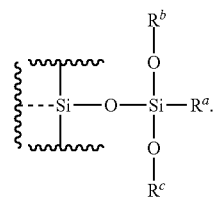

If the silicon nanoparticles contain silane-modified silicon groups of structure

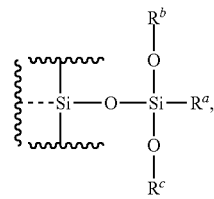

then the silicon nanoparticles optionally can include further modification of silane groups such as, for example, groups of structure

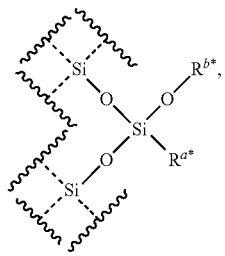

and/or groups of structure

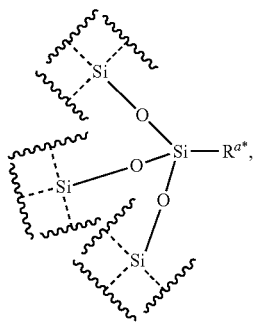

and/or groups of structure

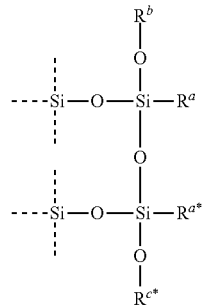

and/or similar branched modifications of silane groups, in which $R^{a*}$, $R^{b*}$ and $R^{c*}$, independently of one another, are optionally substituted residues, selected from the group consisting of H, alkyl, aryl, heteroaryl, cycloalkyl, cycloheteroalkyl, alkenyl and alkoxyalkyl.

As used herein, "substituted alkyl residue" means alkyl residues in which at least one H has been replaced with a suitable substituent. A substituted alkyl residue can contain at least one, for example, 2, 3, 4, 5, 6, 7, 8, 9, 10, 11 or 12 substituents, where, if more than one substituent is present, the substituents present can be identical or different. With regard to the nature of the substituents, in principle there are no restrictions, provided that when the nanoparticles are used, a coating with sufficient hydrophilicity and stability can be provided. The substituents can be, for example, selected from epoxy, aryl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonate, phosphinate, phosphoric acid ester, amino, acylamino, alkylcarbonylamino, arylcarbonylamino, carbamates, carbamides, amidine, nitro, imino, SH, alkylthio, arylthio, thiocarboxylate, sulphate, alkylsulphinyl, sulphonate, sulphamoyl, sulphonamido, trifluoromethyl, cyano, azido, aldehyde, keto group, cycloalkyl (e.g., cyclopentyl or cyclohexyl), heterocycloalkyl (e.g., morpholino), piperazinyl or piperidinyl, and glycosyl. In certain instances, the substituents are hydroxyl groups, glycosyl groups and phosphoric acid ester groups.

As used herein, "cycloalkyl" means optionally substituted, cyclic alkyl residues, wherein they can be monocyclic or polycyclic groups. Optionally substituted cyclohexyl may be mentioned as a particular cycloalkyl residue.

As used herein, "cycloheteroalkyl" means optionally substituted, cyclic alkyl residues, which have at least one heteroatom, such as O, N or S in the ring, where the residues can be monocyclic or polycyclic groups.

As used herein, "substituted cycloalkyl residue" or "cycloheteroalkyl" means cycloalkyl residues or cycloheteroalkyl residues, in which at least one H has been replaced with a suitable substituent. A substituted cycloalkyl residue or cycloheteroalkyl residue can include at least one, for example 2, 3, 4, 5, 6, 7, 8, 9, 10, 11 or 12 substituents, where, if more than one substituent is present, the substituents present can be identical or different. With regard to the nature of the substituents, reference is made to the substituents mentioned as examples with respect to substituted alkyl residues.

As used herein, "aryl" means optionally substituted, 5- and 6-membered aromatic rings, and substituted or unsubstituted polycyclic aromatic groups (aryl groups) such as, for example, tricyclic or bicyclic aryl groups. Optionally substituted phenyl groups or naphthyl groups may be mentioned as examples. Polycyclic aromatic groups also can include non-aromatic rings.

As used herein, "heteroaryl" means optionally substituted, 5- and 6-membered aromatic rings, and substituted or unsubstituted polycyclic aromatic groups such as, for example, tricyclic or bicyclic aryl groups, containing one or more, for example, 1 to 4, such as 1, 2, 3 or 4, heteroatoms in the ring system. If more than one heteroatom is present in the ring system, the at least two heteroatoms that are present can be identical or different. Examples of heteroaryl residues include, but are not limited to, benzodioxolyl, pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, benzoxazolyl, benzodioxazolyl, benzothiazolyl, benzimidazolyl, benzothiophenyl, methylene-dioxyphenylyl, naphthyridinyl, quinolinyl, isoquinolinyl, indolyl, benzofuranyl, purinyl, benzofuranyl, deazapurinyl or indolizinyl.

As used herein, "substituted aryl residue" or "heteroaryl residue" means aryl residues or heteroaryl residues, in which at least one H has been replaced with a suitable substituent. A substituted aryl residue or heteroaryl residue can include at least one, for example, 2, 3, 4, 5, 6, 7, 8, 9, 10, 11 or 12 substituents, where, if more than one substituent is present, the substituents present can be identical or different. With regard to the nature of the substituents, in principle there are no restrictions, provided that the nanoparticle composition has sufficient hydrophilicity and/or a sufficiently stable coating can be provided with the composition. Examples of such substituents include, but are not limited to, aryl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonate, phosphinate, phosphoric acid ester, amino, acylamino, alkylcarbonylamino, arylcarbonylamino, carbamates, carbamides, amidine, nitro, imino, SH, alkylthio, arylthio, thiocarboxylate, sulphate, alkylsulphinyl, sulphonate, sulphamoyl, sulphonamido, trifluoromethyl, cyano, azido, cycloalkyl (e.g., cyclopentyl or cyclohexyl), heterocycloalkyl (e.g., morpholino), piperazinyl or piperidinyl, sugar residues and heteroaryl.

As used herein, "alkoxyalkyl" means alkyl residues that include one or more —O— groups within the alkyl chain. The term also includes groups of alkyl-O-alkyl structure and similar structures, where the respective alkyl residues can be substituted or unsubstituted.

As used herein, "alkenyl" means alkyl residues that have at least one C—C double bond. Regarding the nature of possible substituents, reference is to be made to the foregoing.

In certain instances, $R^a$, $R^b$ and $R^c$ are selected, independently of one another, from H, optionally substituted alkyl residues and optionally substituted alkyoxyalkyl residues.

In view thereof, it is further contemplated that an analytical aid as described herein includes a surface coated at least partially with a hydrophilic coating, where the hydrophilic coating contains nanoparticles with silica structure, which include groups of structure (I), wherein R is

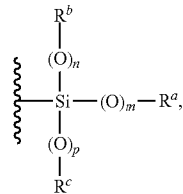

where $R^a$, $R^b$ and $R^c$, independently of one another, are selected from H, optionally substituted alkyl residues and optionally substituted alkyoxyalkyl residues.

Such an analytical aid can be made via a coating step with a mixture G that includes at least one dispersant and nanoparticles with silica structure, as described above, where the nanoparticles have groups of structure (I), where R is

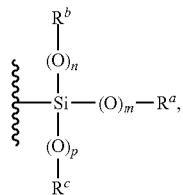

and where $R^a$, $R^b$ and $R^c$, independently of one another, are selected from H, optionally substituted alkyl residues and optionally substituted alkyloxyalkyl residues.

The following groups are examples of the residues $R^a$, $R^b$ or $R^c$:

Examples of silica nanoparticles modified with groups of structure

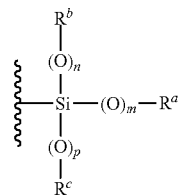

can be modified with the following silanes: octyltriethoxysilane, methyltrimethoxysilane, methyltriethoxysilane, methyltriisopropoxysilane, isocyanate silane, beta-(3,4-epoxycyclohexyl)-ethyl-trimethoxysilane; epoxy-silanes or silanes that have a glycidoxy- and/or a glycidoxypropyl group, such as gamma-glycidoxypropyltrimethoxysilane, gamma-glycidoxypropyltriethoxysilane, gamma-glycidoxypropylmethyldiethoxysilane, 3-glycidoxypropyl-hexyltrimethoxysilane, beta-(3,4-epoxycyclohexyl)-ethyltriethoxysilane, silanes that contain a vinyl group, such as vinyltriethoxysilane, anhydride silanes (i.e., silanes that bear a cyclic organic anhydride unit, e.g., succinic anhydride or maleic acid anhydride), and hydrolysis products thereof, and/or aminosilanes such as 3-aminopropyltri(m)ethoxysilane and di-triaminosilanes.

Alternatively, $R^a$, $R^b$ and $R^c$, independently of one another, can be selected from H, alkyl and groups of the following formulae:

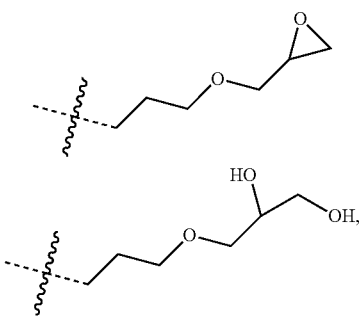

where the alkyl group can be methyl or ethyl, and is ethyl.

In some instances, p and n are 1 and m=0, and $R^b$ and $R^c$ are methyl or ethyl, or just ethyl. In other instances, $R^c$ is

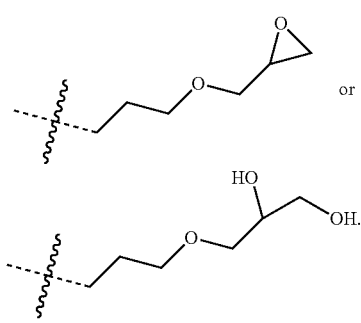

It is further contemplated that an analytical aid as described herein includes a surface coated at least partially with a hydrophilic coating, where the hydrophilic coating contains nanoparticles with silica structure, which include groups of structure (Ia) or structure (Ib):

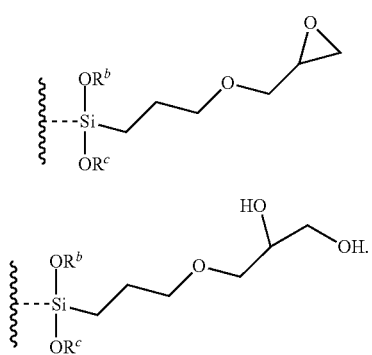

Such an analytical aid can be made via a coating step with a mixture G that includes at least one dispersant and nanoparticles with silica structure, as described above, where the nanoparticles have groups of structure (Ia) or structure (Ib):

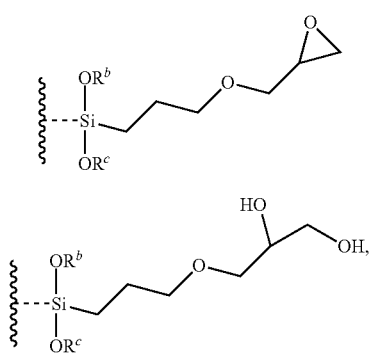

and where $R^b$ and $R^c$, independently of one another, are selected from H and alkyl, or alternatively are selected from H, methyl and ethyl.

The nanoparticles are obtainable, for example, under the name Bindzil® CC30 or CC301 and CC40 or CC401 (EKA Akzo Nobel).

If the nanoparticles contain groups of structure (I), in which R is

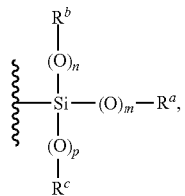

then about 10% to about 50% of all R's of the groups present in the silicon nanoparticle

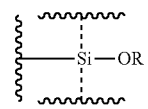

have the structure of formula

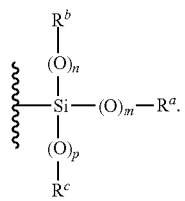

The remaining 50% to 90% of the R's contained in the nanoparticle therefore are H and/or a metal-containing ion and/or

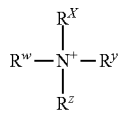

depending on which counter-ion was used for stabilizing the nanoparticles. The remaining groups R, as described above, are H and/or $Na^+$.

It is further contemplated that an analytical aid as described herein includes a surface coated at least partially with a hydrophilic coating, where the hydrophilic coating contains nanoparticles with silica structure, which include groups of structure

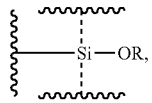

and where about 5% to about 50% of all R's have a structure of

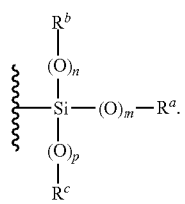

Such an analytical aid can be made via a coating step with a mixture G that includes at least one dispersant and nano particles with silica structure, as described above, where the nanoparticles have groups of structure

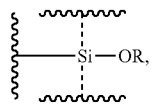

and where preferably about 5% to about 50% of all R's have a structure of formula

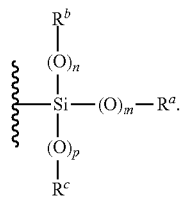

Groups of Structure (II):

As also noted above, the silica nanoparticles can have, additionally or alternatively to the groups of structure (I), groups of structure (II)

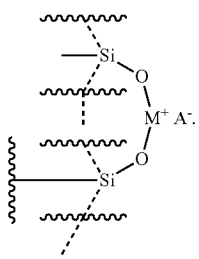

In particular, the nanoparticles have either groups of formula (I) or groups of formula (II) (i.e., when the nanoparticles have groups of formula (I), preferably they have no groups of formula (II), and vice versa).

Here, M is a metal such as, for example, a trivalent metal like aluminium. In some instances, M is aluminium or $M^+ = Al^+$.

In view thereof, an analytical aid as described herein can include a surface coated at least partially with a hydrophilic coating, in which the hydrophilic coating contains nanoparticles with silica structure, where the nanoparticles include groups of structure (IIa)

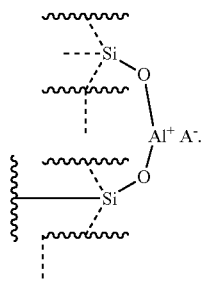

Such an analytical aid can be made via a coating step with a mixture G that includes at least one dispersant and nano-particles with silica structure, as described above, where the nanoparticles have groups of structure (IIa)

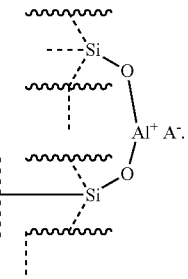

With regard to the chemical nature of the anion $A^-$, there are no restrictions in this respect, provided that anion A– is physiologically compatible and does not falsify the result when the analytical aid is used. Examples of anions include, but are not limited to, chloride (Cl), bromide (Br), iodide (I), sulphate ($SO_4^{2-}$), hydrogen sulphate ($HSO_4$), phosphate ($PO_4^{3-}$) and hydrogen phosphate ($HPO_4^{2-}$). In some instances, anion $A^-$ is Cl.

It therefore is contemplated that an analytical aid as described herein can include a surface coated at least partially with a hydrophilic coating, in which the hydrophilic coating contains nanoparticles with silica structure, where the nanoparticles include groups of structure (IIa)

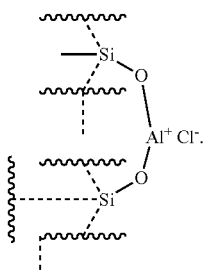

Such an analytical aid can be made via a coating step with a mixture G that includes at least one dispersant and nanoparticles with silica structure, as described above, where the nanoparticles have groups of structure (IIa)

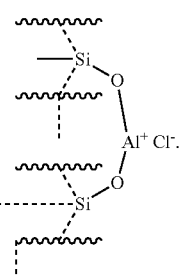

Nanoparticles containing groups of structure (IIa) are obtained by, for example, treatment of nanoparticles with aluminium chloride. Alternatively, such nanoparticles are commercially available as Bindzil® CAT (Akzo Nobel).

Silica Structures:

The nanoparticles have a silica structure, particularly that of an amorphous silica. In addition to Si and O and the groups R or M⁺, the nanoparticles can have further foreign atoms. These foreign atoms include, but are not limited to, Al, B, Ga, Ge, Hf, In, P, Sn, Ti or Zr. If present, the foreign atoms can replace one or more Si atoms in the silica structure. In some instances, the nanoparticles contain Al as foreign atom.

It therefore is contemplated that an analytical aid as described herein can include a surface coated at least partially with a hydrophilic coating, in which the hydrophilic coating contains nanoparticles with silica structure, where the silica structure of the nanoparticles has at least one foreign atom selected Al, B, Ga, Ge, Hf, In, P, Sn, Ti or Zr, particularly Al.

Such an analytical aid is made via a coating step with a mixture G that includes at least one dispersant and nanoparticles with silica structure, as described above, where the silica structure of the nanoparticles has at least one foreign atom selected from Al, B, Ga, Ge, Hf, In, P, Sn, Ti or Zr, particularly Al.

If the silica structure of the nanoparticles contains at least Al, then the nanoparticles contain Al in an amount in the range from about 0.1 wt % to about to 10 wt. %, relative to the total weight of the nanoparticle.

Methods of Producing Analytical Aids:

With respect to coating an analytical aid by bringing the analytical aid into contact with mixture G, the coating can be carried out by any method known to one of skill in the art.

In some instances, the bringing into contact takes place by dip coating, spray coating and/or contact coating. Alternatively, or additionally, however, numerous other methods may be considered. Examples of such methods include, but are not limited to, dip coating, spray coating, spin coating, a pressing process, a knife process or a dropping process. Combinations of these methods and/or other methods also can be used.

Mixture G:

With respect to mixture G that is used in the methods, it includes nanoparticles and at least one dispersant, where the nanoparticles are dispersed or are in the form of a colloidal solution in the at least one dispersant such as, for example, water.

In some instances, mixture G also can include at least one solvent such as, for example, at least one organic solvent including, but not limited to, a polar organic solvent, a polar, protic organic solvent, or an alcohol. In certain instances, the at least one organic solvent is miscible with water. Examples of organic solvents include, but are not limited to, methanol, ethanol, 1-propanol, 2-propanol, methoxymethanol, methoxyethanol and ethylene glycol. If mixture G includes the at least one organic solvent, the solvent mixture contains at most about 50 vol. % of the organic solvent, at most about 0.1 vol. % to about 30 vol. %, at most about 1 vol. % to about 20 vol. %, or at most about 1.5 vol. % to about 5 vol. %, relative to the total volume of mixture G. In particular, mixture G contains at least one solvent in an amount of at most about 50 vol. %.

With respect to the amount of nanoparticles, mixture G contains the nanoparticles in an amount in the range from about 0.01 wt. % to about 5 wt. %, from about 0.02 wt. % to about 3 wt. %, or from about 0.05 wt. % to about 2 wt. %, relative to the total weight of mixture G. In particular, mixture G contains the nanoparticles in an amount in the range from about 0.01 wt. % to about 5 wt. %, relative to the total weight of mixture G.

In some instances, mixture G consists essentially of the at least one dispersant and the nanoparticles with silica structure. As used herein, "essentially" means that the mixture has further constituents, such as impurities, in an amount of at most about 1 wt. %, but alternatively in an amount of at most about 0.1 wt. %.

If the coating step takes place by dip coating, then the dwell time of the analytical aid immersed in mixture G is a maximum of about 5 minutes, about 2 minutes, or about 1 minute. Alternatively, the dwell time can be from about 1 second to about 30 seconds.

The method described above for producing the analytical aid additionally comprises, apart from the steps described above:

A drying step of the analytical aid obtained according to the step above. As used herein, "drying" means that the dispersant present on the analytical aid and any other solvent present is removed essentially completely, preferably completely. Drying can be carried out in a drying cabinet at a predetermined temperature of about 20° C. to about 150° C., about 20° C. to about 120° C., or about 20° C. to about 80° C. Additionally, or alternatively, drying can take place by flow of a gas such as, for example, air, across or through the analytical aid.

In other instances, drying can take place by storing the coated analytical aid in air or in an inert atmosphere at a temperature in the range from about 20° C. to about 150° C., about 20° C. to about 80° C., or at room temperature.

The drying step also can include an additional washing step. As such, the analytical aid obtained according to the step above is first dried, and then washed with a solvent or solvent mixture such as water, where the washing can be carried out for a time of a maximum of about 1 minute, or from about 1 second to about 30 seconds. Following this optional washing step, the analytical aid can be dried again, where the solvent or solvent mixture that was used for washing and is present on the analytical aid is removed essentially completely, preferably completely. The drying steps can be carried out in the same way or differently. In some instances, no washing step is carried out in the drying step.

After the drying step, the analytical aid obtained above optionally can be sterilized. Examples of sterilization methods include, but are not limited to, irradiation with gamma radiation and/or beta radiation. Further possibilities that can be employed alternatively or additionally are steam sterilization and/or autoclaving and/or chemical sterilization with, for example, ethylene oxide (EtO). Generally, at least one sterilization method can be used such as radiation sterilization, in particular with gamma radiation and/or beta radiation; thermal sterilization, in particular dry thermal sterilization and/or steam sterilization; chemical sterilization with at least one germicidal medium, in particular a gaseous; and/or liquid germicidal medium.

In some instances, the analytical aids as described herein can be packed in suitable containers such as, for example, plastic bags, where packing can be effected for example by heat sealing. In this manner, the sterilization step takes place after packing or heat sealing of the analytical aids by, for example, irradiation with gamma radiation.

In some instances, the analytical aid can be treated before the coating step with at least one etchant and/or plasma. In certain instances, the analytical aid can be etched with an etchant before or shortly before the coating step. As used herein, "shortly before" means a time interval not exceeding about 12 hours, not exceeding about 8 hours, not exceeding about 1 hour, or not exceeding about 10 minutes. Thus, for example, a freshly etched analytical aid can be used in the coating step. As used herein, "freshly etched analytical aid" means an analytical aid that has been etched lightly on the surface with an etchant shortly before the treatment with mixture G. It is freshly etched if the time that elapses between etching of the analytical aid and treating the analytical aid with mixture G is a maximum of about 0 hours to about 12 hours, a maximum of about 0 hours to about 8 hours, a maximum of about 0 hours to about 4 hours, a maximum of about 0 hours to about 1 hour, or not more than about 10 minutes.

The analytical aid, optionally etched and then optionally washed with water, is kept in this interval between etching and coating in, for example water that can include a stabilizer. Optionally, the analytical aid is dried before the coating step. Regarding the conditions for drying, reference should be made to the foregoing.

Etching can be carried out, for example, with an etchant that includes nitric acid or an iron(III) chloride solution and hydrochloric acid. If nitric acid is used, it can be in an amount from about 20-wt. % to about 40-wt. %, from about 25-wt. % to about 35-wt. %, or from about 30-wt. % to about 34-wt. % nitric acid.

In some instances, if the surface can be etched as described above, the analytical aid is treated with plasma shortly before the coating step. Thus, an analytical aid freshly treated with plasma can be used in the coating step. As used herein, "analytical aid freshly treated with plasma" means an analytical aid that was treated with plasma shortly before the treatment with mixture G. It is freshly treated with plasma if the time interval between treatment of the analytical aid with plasma and treatment of the analytical aid with mixture G is a maximum of about 0 to about 12 hours, a maximum of about 0 hours to 8 about hours, a maximum of about 0 hours to about 4 hours, a maximum of about 0 hours to about 1 hour, or not more than about 10 minutes.

Hydrophilic Coatings:

As used herein, "hydrophilic coating" means a coating whose surface has, in comparison with the uncoated surface of the analytical aid, a smaller contact angle with water of about at least 15° smaller, measured according to DIN 55660.2 or DIN EN 828:1997. In some instances, the surface of the coating has a contact angle with water of less than about 60°, less than about 50°, less than about 40°, or less than about 30°, as measured according to DIN 55660.2 or DIN EN 828:1997.

Regarding the quantity of nanoparticles on the surface of the analytical aid, the analytical aid can be coated with a quantity of nanoparticles in the range from about 7.5 µg/mm² of surface area of the analytical aid to about 150 ng/mm² of surface area of the analytical aid.

In some instances, at least about 90-wt. %, at least about 95-wt. %, at least about 96-wt. %, at least about 97-wt. %, at least about 98-wt. %, at least about 99-wt. %, at least about 99.5-wt. %, at least about 99.9-wt. %, or about 100-wt. %, of the hydrophilic coating consists of nanoparticles with silica structure.

In some instances, the coatings can contain mixtures of different nanoparticles; however, the coatings also can contain only nanoparticles of one structure.

In some instances, the surface of the analytical aid can be coated partially or completely with the hydrophilic coating. For example, the surface that faces the sample when using the analytical aid can be coated at least partially or completely. In this manner, at least about 80%, at least about 90%, at least about 95%, at least about 98%, or at least about 99% of the surface is coated.

If the analytical aid is incorporated into, for example, a needle element with at least one internal space such as, for example, at least one cannula and/or at least one capillary, then the whole surface of the internal space of the needle element can be provided with a hydrophilic coating. In some instances, the at least one capillary-active surface structure can be coated from a tip of the needle element up to an optional contact point of the needle element with at least one optional testing element with at least one test chemistry for detecting at least one analyte in a body fluid.

Surface of Analytical Aids:

Regarding the chemical nature of the analytical aid, its surface can consist at least partially of a metal, a metal alloy, a metal oxide and/or a mixed metal oxide. In this manner, the analytical aid consists per se of a metal, a metal alloy, a metal oxide and/or a mixed metal oxide. Alternatively, the analytical aid can be produced at least partially from another material, and this material is coated at least partially with a metal, a metal alloy, a metal oxide and/or a mixed metal oxide. In some instances, the analytical aid therefore includes a coating of metal, metal alloy, metal oxide and/or mixed metal oxide.

The coating of metal, metal alloy, metal oxide and/or mixed metal oxide can be applied in any known way. Examples of such methods include, but are not limited to, sputtering, vacuum metallization, galvanic coating or deposition from dissolved metal compounds. Moreover, several layers of metal, metal alloy, metal oxide and/or mixed metal oxide can be applied.

In some instances, the analytical aid can be a testing element or a distributing element and can be coated by vacuum metallization with, for example, Al. The analytical aid thus obtained is then converted by oxidation to a metal oxide and/or a mixed metal oxide, in particular to boehmite. The oxidation is effected with, for example, water, alkali-metal or alkaline-earth metal hydroxides, oxygen, hydrogen peroxide, ozone, heat in the presence of the oxygen of the air or sulphur compounds. In this manner, the metallic surface is at least partially oxidized by the boehmite process with hot water and/or steam.

If such a coating is applied, then this coating containing metal, metal alloy, metal oxide and/or mixed metal oxide is applied on the analytical aid before the coating step.

If the analytical aid is a needle element, the analytical aid preferably is not coated with a metal and/or a metal alloy and/or a metal oxide and/or a mixed metal oxide and/or a mixed metal oxide.

When the nanoparticles include groups of structure (I)

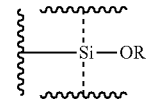

in which R is a metal-containing ion, or is

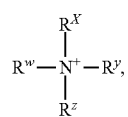

the nanoparticles are de-ionized before the coating step. During de-ionizing, the nanoparticles, containing the groups of structures

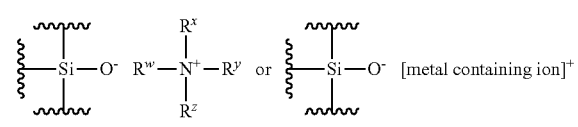

are converted to nanoparticles with groups of structure

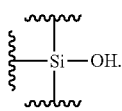

The de-ionizing can be by any method known by one of skill in the art. For example, the de-ionizing can be effected by ion exchange chromatography or by bringing into contact with an acidic ion exchange material.

It therefore is contemplated that an analytical aid as described herein can include a surface coated at least partially with a hydrophilic coating, in which the hydrophilic coating contains nanoparticles with silica structure, where the nanoparticles include groups of structure

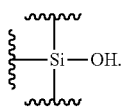

In view thereof, a method of producing an analytical aid as described herein can include the steps of:
(a) providing the analytical aid;
(a1) providing nanoparticles with silica structure, which have an average particle size, determined according to DIN ISO 22412:2008, in the range from about 1 nm to about 500 nm, where the nanoparticles have groups

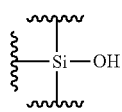

by de-ionizing nanoparticles with silica structure, where the nanoparticles have groups of structure

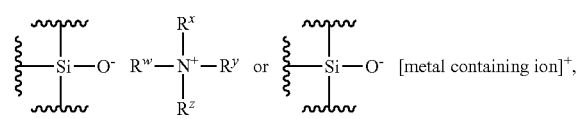

where $R^w$, $R^x$, $R^y$ and $R^z$, independently of one another, are selected from H and alkyl;
(b) coating the analytical aid by bringing the analytical aid into contact with a mixture G comprising at least one dispersant and the nanoparticles obtained according to step (a1);
(c) drying the analytical aid obtained according to step (b); and
(d) optionally sterilizing the analytical aid obtained according to step (c),
wherein the bringing into contact in step (b) takes place by dip coating and/or spray coating and/or contact coating and/or at least one other of the aforementioned methods, and wherein the analytical aid and/or the surface of the analytical aid preferably consists at least partially of a metal and/or a metal alloy and/or a metal oxide and/or a mixed metal oxide and/or a mixed metal oxide.

Analytical Aids:

As used herein, "analytical aid" generally means an element, by means of which or with the aid of which at least one property of at least one sample can be determined. Basically, in this respect any, analytical aids may be considered to be rigid analytical aids or deformable analytical aids. The analytical aid can be completely or partially of a material including, but not limited to, metal, a metal oxide, a paper, a ceramic, a plastic and a textile material such as, for example, cellulose or synthetic fibers. Combinations of the aforementioned materials and/or other materials are also conceivable.

In particular, the analytical aid can be an analytical aid for qualitative and/or quantitative analysis of samples.

The sample can be a liquid or gaseous sample. In some instances, the sample includes at least one body fluid or portions thereof, in particular blood or blood constituents, interstitial fluid, saliva or urine.

The at least one property can be any chemical, physical or biological property. In some instances, the at least one property includes a concentration of at least one analyte in the sample, in particular of at least one metabolite such as, for example, glucose, lactate or cholesterol.

The analytical aid therefore can be an analytical aid used in the context of detecting at least one analyte in a liquid, in particular a body fluid. In some instances, the analytical aid can be an analytical aid used during sampling such as, for example, when collecting a sample of a body fluid, and/or during analysis of the sample in the detection of at least one analyte in a body fluid. In certain instances, the analytical aid can be an analytical aid or a part of an analytical aid for qualitative and/or quantitative analysis of blood and/or interstitial fluid.

More specifically, the analytical aid can be for measuring and/or for the qualitative and/or quantitative detection of at least one analyte of the body fluid such as, for example, sugar such as glucose, lipids, metabolic products (e.g., urea or uric acid), proteins, peptides and salts, or other constituents of the blood or of the interstitial fluid. The at least one analyte to be detected can be, for example, at least one metabolite, glucose, lactate, cholesterol or other metabolites.

Regarding the nature of the analytical aid, all analytical aids known to one of skill in the art are included. Examples of analytical aids include, but are not limited to, a needle element, a testing element for detecting at least one analyte in a liquid, and optionally a distributing element for distributing a sample of a body fluid that has been collected.

Testing Elements:

As used herein, "testing element" or "testing elements" means all carrier-bound elements for detecting at least one analyte in a liquid. A testing element can be for detecting at least one analyte for medical or non-medical purposes. These carrier-bound testing elements generally include one or more layers, containing at least one detection reagent for detecting the at least one analyte of interest. The detection reagents can be incorporated into corresponding layers of a carrier. Bringing the testing element and the detection reagent in contact with the liquid leads, in the presence of the at least one analyte to be detected (also called the target analyte), to a detectable change such as, for example, a physical and/or chemical change by formation of covalent, non-covalent or complex bonds between the detection reagent and the target analyte. This leads to a measurable signal such as, for example, an electrical signal and/or a color change, preferably to a measurable optical signal, which can be evaluated visually or by means of equipment by reflection photometry or fluorescence photometry.

Regarding the outward appearance of the testing element, all outward appearances familiar to one of skill in the art are included in this context. In particular, the testing element can be a test strip, a test tape or a test disk. Without restriction of further, alternatively or additionally usable embodiments, in particular flat, strip-shaped testing elements (i.e., test strips) are described below by way of example.

In addition to the at least one detection reagent, which can carry out at least one analyte-specific reaction, the testing element can include additional substances such as, for example, carriers, excipients, pigments, fillers, buffer substances and the like. In the following, no distinction will be made between further substances that also participate in the reaction for detecting the analyte, and the actual detection reagent. In particular, the detection reagent can comprise an enzymatic detection reagent. As examples of glucose-specific enzymatic detection reagents of this kind, oxidoreductase enzymes (e.g., GlucDOR/PQQ), dehydrogenase enzymes, oxidase enzymes or similar enzymes as mentioned including glucose oxidase (GOD) or glucose dehydrogenase.

The at least one detectable reaction is, as already noted, preferably an optically detectable reaction. However, other types of reactions are contemplated. In particular, it can be a reaction in which, if the at least one target analyte is present, at least one detection substance is formed. Several detection substances also can be formed and/or used, which can be detected individually, in groups or all of them. Detection substances are thus substances that form as a result of the at least one detection reaction and/or take place in the at least one detection reaction and are detectable. Based on the at least one detection substance that is detected, the at least one analyte can be detected quantitatively and/or qualitatively. However, detections and/or detection substances are also possible, for which detection of the at least one detection substance is not used or is not only used for detection of the analyte, but alternatively for example for determining the volume layer of the sample thickness above the test field, as will be described below.

Preferably, the test chemistry described above for detecting the at least one target analyte with at least one detection reagent is not sensitive to the hydrophilic coating. This ensures that if traces of the hydrophilic coating become detached when using the analytical aid, the testing element can be contaminated without affecting the test chemistry. Therefore, owing to the insensitivity of the test chemistry to the coating, the test for detecting the at least one target analyte is not, or is only insignificantly, falsified by traces of the compound of structure (I) or degradation products thereof. Preferably, during use for determination, essentially no, more preferably no, proportion of the hydrophilic coating becomes detached from the analytical aid.

Regarding the structure of the testing element, it has at least one carrier element, in particular a carrier strip. The carrier element can comprise, for example, a plastic material, a ceramic material, a paper material, a composite material or similar. The test field then can be applied on this carrier element. In this manner, the carrier element can be used for providing a mechanically supporting function for the testing element to enable the testing element to be held during sample application and/or during a measurement. As described above, the at least one hydrophilic coating can be applied completely or partially on the carrier element and/or in particular on the test chemistry and/or on one or more other elements of the testing element.

The carrier element can include at least one film element, in particular at least one plastic film. The film element has a closed surface, which is essentially impermeable to the sample. In some instances, the film element is of non-porous design, has a non-porous surface or has pores with an average pore radius of not more than about 5 µm or of not more than about 1 µm. Therefore, the film element differs from conventional network-like materials such as, for example, spreading networks. Generally, the carrier element and/or the carrier surface can have at least one material that is essentially impermeable to the sample.

Distributing Elements:

As used herein, "distributing element" means a device with which a sample received such as, for example, a liquid sample, can be distributed over a two-dimensional distribution region and/or a three-dimensional distribution volume. In particular, for uniform, extensive and rapid distribution of the sample to be analysed, such as small blood samples, the distributing element can be arranged on testing elements such as test strips, in particular, glucose test strips.

Examples of distributing elements include, but are not limited to, a capillary structure, a membrane, a network such as a spreading network. In some instances, the distributing element is a spreading network. As used herein, "membrane" means a porous element such as, for example, a porous film or porous layer, which is arranged to take up the sample and distribute it laterally (i.e., parallel to a plane of the film or layer). In some instances, the membrane includes at least one porous plastic film. As used herein, "spreading network" means a generic term for all filament structures suitable for purposes of spreading or distribution or transfer. This includes, among others, textiles, knitted fabrics and fleeces. As used herein, "filament" means both mono- and poly-filaments of uniform or non-uniform material basis and dimensioning. It should be mentioned that sample transfer preferably takes place through the filament structure.

In some instances, the membrane and/or the spreading network lie on at least one layer of a testing element such as, for example, a detection layer of the testing element, containing the at least one detection reagent and/or a separating layer containing at least one reflecting pigment and/or at least one substance that is arranged for separating sample constituents such as, for example, red blood cells. The applied sample liquid thus can be led by the spreading network by capillary action to the layer containing the at least one detection reagent and, at the points of contact of the spreading network and detection layer, can be spread or distributed, also by capillary forces, on the detection layer. In this manner, the spreading network serves as an aid for undirected (isotropic) two-dimensional distribution of a liquid sample at the target location, namely on the at least one layer containing the at least one detection reagent. The desired intermediate storage and superficial spreading of the sample only occur in interaction with the spreading network, with the spreading network demarcating, with respect to the detection layer, a large number of varying capillary-active interstices or capillary gaps, which owing to the surface contour of the filaments and the spatial arrangement thereof, are largely undirected overall.

As described above, the surface of the analytical aid can include a metal, a metal alloy, a metal oxide and/or a mixed metal oxide. Accordingly, the analytical aid can be a distributing element including a surface consisting of metal, metal alloy, metal oxide and/or mixed metal oxide. In some instances, the analytical aid is a distributing element such as, for example, a spreading network, which can be coated with metal, metal alloy, metal oxide and/or mixed metal oxide, as described above.

In view thereof, it therefore is contemplated that an analytical aid as described herein can include a spreading network that is optionally coated with metal, metal alloy, metal oxide and/or mixed metal oxide.

Needle Elements:

In some instances, the analytical aid can be a needle element or can include a needle element. In this manner, the needle element can be any element with a tip or blade, which is arranged for producing an opening in a portion of a user's skin. Examples of needle elements include, but are not limited to, a lancet, a cannula such as a hollow cannula or an at least partially open hollow cannula, a microcutter or the like, and a capillary such as a capillary gap.

If the needle element is a lancet, the lancet can include a so-called microsampler (i.e., an element that has both a tip and/or blade for producing a puncture and at least one capillary channel for taking up the sample). In addition, the microsampler optionally can include at least one testing element for detecting at least one analyte in the sample.

In general, the needle element can have at least one capillary-active surface structure, which also is simply called capillary structure in the following and which need not necessarily be arranged completely on a surface of the needle element. In particular, the capillary structure can have at least one capillary channel and/or at least one capillary trough. Owing to the capillary action of the surface structure, the body fluid flowing from the puncture site can be taken up by the capillary structure and can be transported to a testing element arranged on the needle element. The capillary structure can provide a receiving volume for receiving an amount of body fluid required for one or more tests. The surface structure can be formed by at least one capillary trough running parallel and/or at least partially transversely to the longitudinal axis of the needle element. With capillary troughs running parallel to the longitudinal axis of the needle element, it is contemplated that a number of capillary troughs from, for example, about 2 to about 6 or about 2 or 3, can be used. However, it also is contemplated that up to about 10 capillary troughs to be formed on the needle element. With a hollow cannula, the capillary structure is formed by the hollow shape of the cannula.

The possibility of targeted uptake and/or targeted transport of body fluid out of or from the puncture site is advantageous in the design of the capillary structures. For example, transport can take place to at least one testing element arranged on or arrangeable on the needle element or to the needle element. The testing element can be arranged fixed to the needle element and/or the capillary structure, but it also can be mounted movably to these so that after uptake of the body fluid into the capillary structure, the testing element moves towards the capillary structure. Advantageously, the hydrophilic coating, plasma treatment and/or formation of nano- and microstructures at least in the capillary troughs, but also on the whole surface, additionally contributes to the capillary action.

Hydrophilic coating of the needle element can be complete or partial as described above. In some instances, the whole surface of the needle element is provided with a hydrophilic coating, as well as the at least one capillary-active surface structure from the tip of the needle element to the needle element/testing element contact point.

If, for example, the body fluid is taken up with the needle element, the body fluid is transported along the needle element within about 30 ms/mm to about 1000 ms/mm of transport distance from the puncture site to the testing element. Alternatively, the time can be within about 40 ms/mm to about 700 ms/mm of transport distance or within 40 ms/mm to about 400 ms/mm of transport distance. As used herein, "transport distance" means the distance that is traveled, preferably can be traveled as a maximum, in the needle element by the sample that is taken up. The total transport distance generally can have a length from about 0.5 mm to about 10 mm or from about 1 mm to about 5 mm. For example, the transport distance can be a total length of a capillary such as, for example, a capillary gap, in the needle element. Alternatively, or additionally, transport distance refers to the length of the needle element from a tip to a discharge opening such as, for example, in the case of a cannula.

At least one testing element with at least one test chemistry for detecting the analyte can be provided, which can be completely or partially a constituent of the needle element, but which also can be formed completely or partially separately from the needle element. If the testing element is not a constituent of the needle element, transfer of the body fluid from the needle element can also take place with a time delay after uptake of the body fluid by the needle element. Until this transfer, a further period of time can elapse such as, for example, a period from about 0.5 s to about 5 s after commencement of puncture and/or after retraction of the needle element from the body tissue, in particular a period from about 1 s to about 2 s.

In some instances, the analytical aid is a needle element of a sampling device for collecting a body fluid.

It therefore is contemplated that an analytical aid as described herein can include a needle element of a sampling device for collecting a body fluid.

Likewise, it is contemplated that a method of producing an analytical aid as described herein can include incorporating the analytical aid as a needle element of a sampling device for collecting a body fluid. As used herein, "sampling device" means a device that is arranged for taking up a sample for the purpose of an analysis. Moreover, the sampling device can be arranged for generating the sample by, for example, making a puncture and/or cut in a skin surface with at least one needle element. Alternatively, or additionally, the sampling device can be arranged for detecting at least one analyte in the sample by, for example, means of at least one testing element as described herein.

Such a sampling device includes at least one analytical aid with at least one surface coated at least partially with a hydrophilic coating, with the proviso that the analytical aid is a needle element or a testing element. With respect to the needle element and/or the testing element, reference may be made to the above description and to the embodiments described hereunder. As noted above, the needle element can include at least one microsampler, which is provided completely or partially with the at least one coating, in particular, in the region of a capillary structure. Likewise, the testing element can include at least one distributing element provided with the hydrophilic coating, such as at least one spreading network provided with the hydrophilic coating, which can be located on at least one test field of the testing element.

The sampling device can therefore have at least one needle element for taking a sample of a body fluid and/or at least one testing element, with which at least one analyte in the respective body fluid can be detected qualitatively and/or quantitatively. The testing element can be connected to the needle element, so that the body fluid can travel from the needle element to the testing element, for example, a sample application point or a sample application surface of the testing element. Alternatively, or additionally, however, the testing element can be arranged as a separate testing element or can be applied in some other way in or on the sampling device such as, for example, in at least one chamber in which the needle element also can be located. A transfer mechanism can be provided, which transfers the body fluid taken up by the needle element to the testing element. This can take place by means of an actuator or some other mechanism whereby the needle element with the body fluid is brought closer to the testing element so that the body fluid is transferred at least partially from the needle element to the testing element such as, for example, a test field of the testing element. In this manner, the needle element and/or at least one capillary structure of the needle element can be placed on the test field. However, other configurations also are contemplated.

So that the body fluid can pass from the capillary-active surface structure into the testing element, the testing element can be constructed at a connecting point between testing element and surface structure, so that the body fluid is transferred by suction from the surface structure into the testing element. For this, it is desirable for the testing element to be provided with a capillary-active component (e.g., an absorbent fleece or a fiber bundle) whose capillary action is greater than the capillarity of the surface structure. Alternatively, or additionally, however, it also can be designed so that the capillary is brought into contact with the chemistry by placing the capillary on the chemistry, optionally also with application of pressure. Moreover, contact should be ensured between the surface structure of the cannula and the capillary-active component of the testing element.

In some instances, the sampling device can further include at least one sensor, which can be of electrochemical and/or optical design. With the electrochemical sensor, a substance of the body fluid that is to be determined can be reacted through catalytic action of the test chemistry and this reaction can be measured electrochemically. With the optical sensor, a product of reaction of the test chemistry with a substance contained in the body fluid is irradiated with light of a defined wavelength and a degree of absorption of this light and/or a degree of reflection of the light and/or the fluorescence of the sample are measured.

In some instances, the sampling device can be equipped with a conducting element such as an electrical conducting element. In the case of an electrochemical sensor, this conducting element can be a metal layer applied on a plastic film and/or a metal foil or a metal wire, which is optionally injected into the respective component (e.g., by an injection moulding process). The conducting element also can be formed from conductive plastic or in some other way such as, for example, by means of conductive ink. The sampling device also can have at least one electrical and/or optical contact point, via which the sampling device can be coupled to peripheral equipment. Thus, the sampling device can be supplied with current via an electrical contact point and information can be transferred via the electrical contact point. Light can be transferred between peripheral equipment and the sampling device via an optical contact point In the case of an optical sensor, the sampling device can be equipped both with an electrical and with an optical contact point.

In some instances, the sampling device can be designed completely or partially as a disposable article and/or a multi-use article, where in the case of a disposable article, the sampling device is disposed of after a single use, whereas in the case of a multi-use article, multiple use is intended. Magazining of one or more sampling devices and/or of parts thereof also is contemplated, similar, for example, to the magazining of lancets in lancing aids by storing several sampling devices as a whole in a magazine and/or where a sampling device contains several testing elements and/or several needle elements in magazined form.

As described above, the analytical aid, especially the needle element and/or the testing element, can be produced at least partially from a metal, a metal alloy, a metal oxide and/or a mixed metal oxide. In addition, the material of the needle element and/or of the testing element should be inert, in particular with respect to the body fluid to be sampled, and biocompatible, and mechanically strong as well as easy to sterilize. In some instances, the needle element can be made of surgical steel that can be provided with a coating of metal oxides. Alternatively, or additionally, to a metallic material, the needle element can be completely or partially produced in another material or include another material such as, for example, a plastic material and/or a ceramic material. In certain instances, the needle element is coated with metal, metal alloy, metal oxide and/or mixed metal oxide, and the hydrophilic coating is applied on this surface.

The analytical aids and the methods described herein have a multiplicity of advantages over known analytical aids and methods. Thus, it was surprisingly found that a hydrophilic coating with nanoparticles of the kind described herein result in surface properties with excellent hydrophilicity. In addition, the coating surprisingly is distinguished by good long-term stability, thereby making it possible to ensure stable storage over a relatively long period of time. More specifically, the hydrophilic properties of the coating can be shown to be impaired only marginally, if at all, even by direct or indirect contact with various materials of the analytical aid, such as plastic materials, adhesives or metals for example.

Moreover, strain due to sterilization by, for example, radiation strain caused by β rays and/or γ rays, as well as strain caused by chemical disinfectants such as ethylene oxide, also do not or only marginally impair the hydrophilic properties of the coating. As a result, a long-term stability of about 6-12 months or more can be achieved without problem, while the hydrophilic surface properties are maintained.

Furthermore, the coating described herein is extremely resistant to contaminations and itself does not contaminate a collected sample. Accordingly, the analytical aid may optionally be used multiple times. More specifically, a coating as described herein may be employed in capillary elements and/or channels of the analytical aid, with these elements having long-lasting hydrophilicity due to the coating.

Likewise, the coating described herein can be prepared in a simple and reliable manner. More specifically, the surface coating can be applied, for example, from an aqueous solution and/or an aqueous dispersion. An application method of this kind can easily be carried out.

With respect to FIG. 1, it shows a highly schematic sectional side view of an exemplary sampling device 110. The sampling device 110 includes a needle element 112 with a tip 114, which on movement of the needle element 112 in a puncturing direction 116 pierces a portion of a user's skin. The movement of the needle element 112 can, for example, be driven by an optional actuator 118 of the sampling device 110, which can be arranged in various ways known by one of skill in the art. The actuator 118 can bring about a forward movement of the needle element 112 in the puncturing direction 116 and optionally also a backward movement of the needle element 112 against the puncturing direction.

The needle element 112 optionally can include at least one capillary-active surface structure in the form of a capillary structure 120 having at least one capillary gap, which can extend parallel to the puncturing direction 116. Other embodiments of the capillary structure 120 also are possible. The capillary structure 120 can serve for taking up and/or for transporting a sample of the body fluid in a sampling operation, when the needle element 112 penetrates into a body tissue. For example, transporting or taking-up of the sample can take place by capillary forces.

The needle element 112 further includes at least one hydrophilic coating 122, preferably in the region of the capillary structure 120. The details of the hydrophilic coating 122 and methods of production thereof are explained in more detail above and below.

The sampling device 110 also can include at least one testing element 124 with at least one test chemistry for detecting at least one analyte in the body fluid. For example, the testing element includes at least one test field, thus at least one area coated with the test chemistry. In FIG. 1, the testing element 124 is shown symbolically as testing element 124, formed separately from the needle element 112, and which can be arranged in or on a housing 126 of the sampling device 110, such as for example, a magazine housing.

After a sample is taken up, the needle element 112 with the capillary structure 120 can be brought closer to the testing element 124 to transfer a sample of the body fluid or a portion thereof from the capillary structure 120 to the testing element 124. For this purpose, an actuator 128 can be provided in the sampling device 110, which moves the needle element 112 or a part thereof, after sample uptake, in a direction of movement 130 towards the testing element 124. Alternatively, or additionally, however, there are other possibilities for transferring the body fluid from the capillary structure 120 and/or from the needle element 112 to the testing element 124, for example, by passing the needle element 112, during a backward movement after sample collection, along a suitable path past the testing element 124. Once again, however, it also is possible, alternatively or additionally, to integrate the optional testing element completely or partially in the needle element 112 at one end of the capillary structure 120.

Various examples relating to the production of hydrophilically coated analytical aids are explained below.

EXAMPLES

The invention will be more fully understood upon consideration of the following non-limiting examples, which are offered for purposes of illustration, not limitation.

Example 1

Coating of the Capillaries and Verification of the Shelf Lives of Hydrophilizing Agents Materials Used:
Capillaries with cross-sections of 120×80 μm
Makrolon® 2458 (Bayer) granules coating materials:
1. Ar plasma
2. Heparin
3. Carbopol® 971 PNF (Na salt of a partially cross-linked high-molecular polyacrylic acid) (commercially available from Lubrizol)
4. Mega 8 (octanoyl-N-methylglucamide) (commercially available from Dojindo)
5. DONS (dioctylsodium succinate) (commercially available from Cytec Industries B.V.)
6. PVA 28-99 (polyvinyl alcohol) (commercially available from Fluka)
7. PVP K15 (polyvinyl pyrrolidone) (commercially available from Aldrich)
8. Bindzil® CC30 (nano-silica dispersion) (Akzo Nobel)
9. Ludox® AM-30 (nano-silica dispersion) (commercially available from Aldrich)
10. Ludox® AS-30 (nano-silica dispersion) (commercially available from Aldrich)
11. Bindzil® 2034DI (nano-silica dispersion) (commercially available for example from Akzo Nobel or EKA)
12. CMC (carboxymethyl cellulose, MW=700 000 g/mol, degree of substitution DS 0.9; commercially available from Aldrich)
13. Bindzil® CC301 (nano-silica dispersion) (Akzo Nobel)
14. Bindzil® CC401 (nano-silica dispersion) (Akzo Nobel)
15. Bindzil® 33/360 (nano-silica dispersion) (Akzo Nobel)

General Specification 1(a) for Coating Capillaries: Coating was effected by allowing the aqueous dispersions or solutions of the coating materials to flow purely by capillary forces into the capillaries with cross-sections of 120×80 μm, until the capillaries were completely filled (about 35 nl). Then, the coating was dried briefly with an air blower at room temperature or by heating to 140° C.

Prior to coating, the capillaries were made wettable by a plasma treatment.

General Specification 1(b) for Plasma Treating the Capillaries: The capillaries were treated for 30 s in a plasma stove (Plateg) at 50 mbar argon pressure and 400 W microwave power.

General Specification 1(c) for Sterilization: Sterilization was effected by treatment with beta radiation, 25 kGy.

Example 1.1

Shelf Lives of Hydrophilizing Agents in the Presence of Makrolon®

The shelf lives of the various hydrophilizing agents in the presence of volatile constituents of packaging materials were verified for Makrolon® in each case by heat-sealing 6 capillaries coated according to general specification 1(a), which were treated with plasma prior to coating according to general specification 1(b), with in each case 4 g of granules of Makrolon® 2458 or without granules, in a PET bag and storing them for the specified time. Unless stated otherwise, all bags were sterilized with 25 kGy beta radiation. The time for filling on a length of 4 mm was measured. The measurement was carried out with heparin-blood, HK 44. The results are presented in Table 1.

TABLE 1

| Material | Concentration of solution/dispersion used [in water] (w/w) | Directly after sterilization | Sterilized 8 days/ 75° C. w/o Makrolon ® | Sterilized 8 days/ 75° C. w/ Makrolon ® | Sterilized 21 days/ 75° C. w/ Makrolon ® |
|---|---|---|---|---|---|
| Ar-plasma* | — | <300 ms (w/o sterilization) | does not fill | does not fill | — |

TABLE 1-continued

| Material | Concentration of solution/dispersion used [in water] (w/w) | Directly after sterilization | Sterilized 8 days/ 75° C. w/o Makrolon ® | Sterilized 8 days/ 75° C. w/ Makrolon ® | Sterilized 21 days/ 75° C. w/ Makrolon ® |
|---|---|---|---|---|---|
| Heparin* | 0.05% | — | 300 ms | does not fill | — |
| Carbopol ® 971PNF* | 0.1% | — | 450 ms | 625 ms | about 2100 ms |
| Mega 8* | 0.05% | does not fill | does not fill | does not fill | — |
| DONS* | 0.05% | does not fill | does not fill | does not fill | — |
| PVA 28-99* | 0.05% | about 2000 ms | >2500 ms | about 2000 ms | — |
| PVP K15* | 0.05% | — | 545 ms | 680 ms | — |
| Bindzil ® CC30 | 0.5% | — | 225 ms | 200 ms | 210 ms |
| Ludox ® AM-30 | 0.5% | — | 342 ms | 400 ms | 320 ms |
| Ludox ® AS-30 | 0.5% | — | 270 ms | 240 ms | 260 ms |
| Bindzil ® 2034DI | 0.5% | — | 305 ms | 240 ms | 300 ms |

* not according to the invention

The results show that even after storage in PET bags in the presence of Makrolon®, permit a filling time of less than 400 ms for 4 mm length at a cross-section of 120×80 μm.

Example 1.2

Shelf Lives of Hydrophilizing Agents in the Presence of Zylar®

The shelf lives of the various hydrophilizing agents in the presence of volatile constituents of packaging materials also were verified for Zylar®, which contains a higher proportion of volatile substances compared with Makrolon®, by storing in each case 6 capillaries coated according to general specification 1(a), which were treated with plasma prior to coating according to general specification 1(b), together with injection mouldings in the material Zylar® 220 (MBS copolymer; Ineos-Nova, about 1.5 mm thick, weight 4 g). The time for filling on a length of 4 mm was measured. Measurement was carried out with heparin-blood, HK 44. The results are presented in Table 2.

TABLE 2

| Material | Concentration silica in water w/w | Directly after sterilization, with Zylar ® 220 | 1 week 75° C. with Zylar ® 220 | 2 weeks 75° C. with Zylar ® 220 |
|---|---|---|---|---|
| Bindzil ® CC301 | 0.5% | <300 | <500 | <700 |
| Bindzil ® CC30 | 0.5% | <300 | <500 | <700 |
| Bindzil ® CC401 | 0.5% | <300 | <500 | <700 |
| Ludox ® AS-30 | 0.5% | <300 | No filling | No filling |
| Ludox ® AM-30 | 0.5% | <300 | No filling | No filling |
| Bindzil ® 30/360 | 0.5% | <300 | No filling | No filling |

In the presence of Zylar®, the coatings with silica nanoparticles modified by organic groups display advantages over the silica nanoparticles with no organic modifications.

Example 1.3

Comparative Example of Shelf Lives of Hydrophilizing Agents in the Presence of Zylar with Non-Inventive Coating By way of a comparative example for comparing coatings as described herein with non-inventive coatings, the exemplary embodiment described in Example 1.2 was repeated once more with non-inventive coatings. The coating material applied here included mixtures of carboxymethyl cellulose (CMC) with DONS, which are coatings that are described in EP 2014727. The coating involved firstly preparing an aqueous solution of CMC, to which the appropriate amount of DONS was added. The aqueous solution obtained was used for coating according to general specification 1(a).

The shelf lives of the particular mixtures of CMC and DONS in the presence of volatile constituents of packaging materials were again determined for the example of Zylar®, according to Example 1.2. The results are presented in Table 3.

TABLE 3

| Material (mass ratio) | Concentration in water w/w | Directly after sterilization, with Zylar ® 220 | 1 week 75° C. with Zylar ® 220 |
|---|---|---|---|
| CMC/DONS (20:1) | 0.05% | <300 | No filling |
| CMC/DONS (10:1) | 0.05% | <300 | No filling |

In the presence of Zylar®, the capillaries having the coatings with CMC and DONS did not fill anymore even after one week.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

LISTING OF REFERENCE NUMBERS

110 Sampling device
112 Needle element
114 Tip
116 Puncturing direction
118 Actuator
120 Capillary structure
122 Hydrophilic coating
124 Testing element
126 Housing
128 Actuator
130 Direction of movement

The invention claimed is:
1. An analytical aid comprising:
a surface coated at least partially with a hydrophilic coating, wherein the hydrophilic coating contains nanoparticles with silica structure and an average particle size in a range from about 1 nm to about 500 nm, wherein the nanoparticles comprise groups of structure (I) or (II):

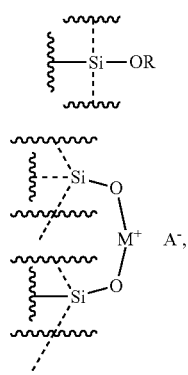

wherein in each of the groups of structure (I), independently of one another, R is selected from the group consisting of H, a metal-containing ion,

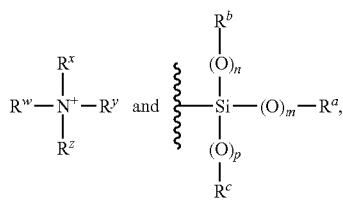

wherein $R^w$, $R^x$, $R^y$ and $R^z$, independently of one another, are selected from H and alkyl, wherein $R^a$, $R^b$ and $R^c$, independently of one another, are optionally substituted residues, selected from the group consisting of H, alkyl, aryl, heteroaryl, cycloalkyl, cycloheteroalkyl, alkenyl and alkoxyalkyl, wherein n, m and p, independently of one another, are 0 or 1, and wherein $M^+$ is a metal ion and $A^-$ is a physiologically compatible anion.

2. The analytical aid of claim 1, wherein R is selected from the group consisting of H, an alkaline-earth metal ion, an alkali metal ion,

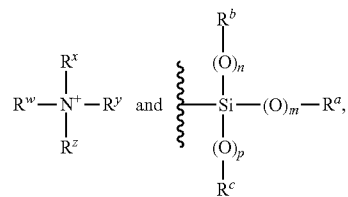

and
wherein $M^+=Al^+$.

3. The analytical aid of claim 1, wherein the silica structure of the nanoparticles has at least one foreign atom selected from the group consisting of Al, B, Ga, Ge, In, Ti, Sn and Zr.

4. The analytical aid of claim 3, wherein the at least one foreign atom is Al.

5. The analytical aid of claim 1, wherein the nanoparticles have an average particle size in the range from about 1 mm to about 100 nm.

6. The analytical aid of claim 5, wherein the nanoparticles have an average particle size in the range from about 1 nm to about 50 nm.

7. The analytical aid of claim 5, wherein the nanoparticles have an average particle size in the range from about 3 nm to about 20 nm.

8. The analytical aid of claim 1, wherein about 10% to about 40% of all groups R are

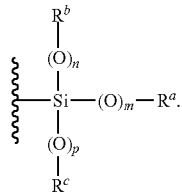

9. The analytical aid of claim 5, wherein the group of structure (I) is structure (Ia) or structure (Ib):

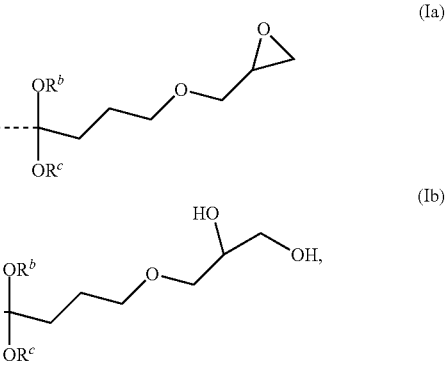

and
wherein $R^b$ and $R^c$, independently of one another, are selected from the group consisting of H and alkyl.

10. The analytical aid of claim 1, wherein the hydrophilic coating consists of the nanoparticles with silica structure.

11. The analytical aid of claim 1, wherein the surface of the analytical aid, coated at least partially with the hydrophilic coating, consists at least partially of one or more of a metal, a metal alloy, a metal oxide or a mixed metal oxide.

12. The analytical aid of claim 1, wherein the nanoparticles have an average particle size in the range from about 1 nm to about 100 nm, and wherein the hydrophilic coating has a thickness.

13. The analytical aid of claim 12, wherein the thickness is an average thickness.

14. The analytical aid of claim 12, wherein the hydrophilic coating has a thickness of about 500 nm.

15. The analytical aid of claim 12, wherein the hydrophilic coating has a thickness in of about 300 nm.

16. The analytical aid of claim 12, wherein the hydrophilic coating has a thickness of about 100 nm.

17. The analytical aid of claim 1, wherein the surface of the hydrophilic coating has a contact angle with water of less than about 50.

18. The analytical aid of claim 1, wherein the analytical aid is selected from the group consisting of a needle element, a capillary, a cannula, a testing element for detecting at least one analyte in a body fluid, and a distributing element for distributing a sample of a body fluid that has been collected.

19. The analytical aid of claim 18, wherein the analytical aid is a needle element, and wherein the needle element is a lancet.

20. The analytical aid of claim 18, wherein the analytical aid is a capillary, and wherein the capillary is a capillary gap.

21. The analytical aid of claim 18, wherein the analytical aid is a distributing element for distributing a sample of a body fluid that has been collected, and wherein the distributing element is a spreading network.

22. The analytical aid of claim 21, wherein the spreading network is coated with one or more of a metal, a metal alloy, a metal oxide, a mixed metal oxide or a plastic film.

23. The analytical aid of claim 22, wherein the spreading network is coated with a plastic film, and wherein the plastic film is coated with one or more of a metal, a metal alloy, a metal oxide and a mixed metal oxide.

24. The analytical aid of claim 1, wherein the analytical aid is a needle element of a sampling device for taking a sample of body fluid.

* * * * *